United States Patent
Sabesan

(10) Patent No.: US 9,918,670 B2
(45) Date of Patent: Mar. 20, 2018

(54) DETECTING SEIZURES BASED ON HEARTBEAT DATA

(71) Applicant: Cyberonics, Inc., Houston, TX (US)

(72) Inventor: Shivkumar Sabesan, Houston, TX (US)

(73) Assignee: Cyberonics, Inc., Houston, TX (US)

( * ) Notice: Subject to any disclaimer, the term of this patent is extended or adjusted under 35 U.S.C. 154(b) by 0 days.

(21) Appl. No.: 15/449,405

(22) Filed: Mar. 3, 2017

(65) Prior Publication Data

US 2017/0172483 A1    Jun. 22, 2017

Related U.S. Application Data

(63) Continuation of application No. 14/262,449, filed on Apr. 25, 2014, now Pat. No. 9,585,611.

(51) Int. Cl.
| | |
|---|---|
| A61B 5/00 | (2006.01) |
| A61B 5/0456 | (2006.01) |
| A61B 5/0205 | (2006.01) |
| A61N 1/36 | (2006.01) |
| A61B 5/024 | (2006.01) |

(Continued)

(52) U.S. Cl.
CPC ........ *A61B 5/4094* (2013.01); *A61B 5/02055* (2013.01); *A61B 5/0456* (2013.01); *A61B 5/7282* (2013.01); *A61N 1/36064* (2013.01); *A61N 1/36139* (2013.01); *A61B 5/024* (2013.01); *A61B 5/0488* (2013.01);
(Continued)

(58) Field of Classification Search
CPC ....... A61B 5/0006; A61B 5/01; A61B 5/0205; A61B 5/024; A61B 5/02405; A61B 5/0456; A61B 5/0488; A61B 5/05; A61B 5/053; A61B 5/1118; A61B 5/4094; A61B 5/4842; A61B 5/4866; A61B 5/7282; A61N 1/36

See application file for complete search history.

(56) References Cited

U.S. PATENT DOCUMENTS

| | | | |
|---|---|---|---|
| 4,702,254 A | 10/1987 | Zabara | |
| 4,867,164 A | 9/1989 | Zabara | |

(Continued)

FOREIGN PATENT DOCUMENTS

| | | |
|---|---|---|
| EP | 2 030 565 | 5/2013 |
| WO | WO-2007/072425 | 11/2007 |
| WO | WO-2013/056099 | 4/2013 |

OTHER PUBLICATIONS

Borovikova, L.V. et al., "Vagus Nerve Stimulation Attenuates the Systemic Inflammatory Response to Endotoxin," Letters to Nature, nature, vol. 405, May 25, 2000, pp. 458-462.

(Continued)

*Primary Examiner* — Amanda Patton
(74) *Attorney, Agent, or Firm* — Foley & Lardner LLP

(57) ABSTRACT

A method includes receiving heartbeat data of a patient and receiving activity data of the patient. The activity data includes one or more activity values that are related to an activity level of the patient and that are measured independently of the heartbeat data. The method further includes determining a value of a weighting factor based on the activity data. The method also includes determining modified heartbeat data by applying the weighting factor to at least a portion of the heartbeat data. The method also includes detecting a seizure event based on the modified heartbeat data.

18 Claims, 4 Drawing Sheets

(51) Int. Cl.
  *A61B 5/0488* (2006.01)
  *A61B 5/053* (2006.01)
  *A61B 5/11* (2006.01)
(52) U.S. Cl.
  CPC .............. *A61B 5/053* (2013.01); *A61B 5/1118* (2013.01); *A61B 5/4809* (2013.01)

(56) References Cited

U.S. PATENT DOCUMENTS

| | | | |
|---|---|---|---|
| 4,920,979 A | 5/1990 | Bullara | |
| 4,979,511 A | 12/1990 | Terry, Jr. | |
| 5,012,411 A | 4/1991 | Policastro et al. | |
| 5,025,807 A | 6/1991 | Zabara | |
| 5,081,987 A | 1/1992 | Nigam | |
| 5,137,020 A | 8/1992 | Wayne et al. | |
| 5,154,172 A | 10/1992 | Terry et al. | |
| 5,179,950 A | 1/1993 | Stanislaw | |
| 5,186,170 A | 2/1993 | Varrichio et al. | |
| 5,188,104 A | 2/1993 | Wernicke et al. | |
| 5,205,285 A | 4/1993 | Baker, Jr. | |
| 5,215,086 A | 6/1993 | Terry, Jr. et al. | |
| 5,215,089 A | 6/1993 | Baker, Jr. | |
| 5,222,494 A | 6/1993 | Baker, Jr. | |
| 5,231,988 A | 8/1993 | Wernicke et al. | |
| 5,235,980 A | 8/1993 | Varrichio et al. | |
| 5,237,991 A | 8/1993 | Baker et al. | |
| 5,263,480 A | 11/1993 | Wernicke et al. | |
| 5,269,302 A | 12/1993 | Swartz et al. | |
| 5,269,303 A | 12/1993 | Wernicke et al. | |
| 5,299,569 A | 4/1994 | Wernicke et al. | |
| 5,304,206 A | 4/1994 | Baker, Jr. et al. | |
| 5,330,507 A | 7/1994 | Schwartz | |
| 5,330,515 A | 7/1994 | Rutecki et al. | |
| 5,335,657 A | 8/1994 | Terry, Jr. et al. | |
| 5,338,657 A | 8/1994 | Kato | |
| 5,458,625 A | 10/1995 | Kendall | |
| 5,522,862 A | 6/1996 | Testerman et al. | |
| 5,531,778 A | 7/1996 | Maschino et al. | |
| 5,540,730 A | 7/1996 | Terry, Jr. et al. | |
| 5,540,734 A | 7/1996 | Zabara | |
| 5,571,150 A | 11/1996 | Wernicke et al. | |
| 5,601,435 A | 2/1997 | Quy | |
| 5,611,350 A | 3/1997 | John | |
| 5,690,681 A | 11/1997 | Geddes et al. | |
| 5,690,688 A | 11/1997 | Noren et al. | |
| 5,700,282 A | 12/1997 | Zabara | |
| 5,707,400 A | 1/1998 | Terry, Jr. et al. | |
| 5,720,771 A | 2/1998 | Snell | |
| 5,743,860 A | 4/1998 | Hively et al. | |
| 5,814,092 A | 9/1998 | King et al. | |
| 5,913,882 A | 6/1999 | King et al. | |
| 5,916,239 A | 6/1999 | Geddes et al. | |
| 5,928,272 A | 7/1999 | Adkins et al. | |
| 5,995,868 A | 11/1999 | Dorfmeister et al. | |
| 6,016,449 A | 1/2000 | Fischell et al. | |
| 6,018,682 A | 1/2000 | Rise | |
| 6,041,258 A | 3/2000 | Cigaina et al. | |
| 6,061,593 A | 5/2000 | Fischell et al. | |
| 6,073,048 A | 6/2000 | Kieval et al. | |
| 6,104,956 A | 8/2000 | Naritoku et al. | |
| 6,205,359 B1 | 3/2001 | Boveja | |
| 6,208,894 B1 | 3/2001 | Schulman et al. | |
| 6,208,902 B1 | 3/2001 | Boveja | |
| 6,221,908 B1 | 4/2001 | Kilgard et al. | |
| 6,240,316 B1 | 5/2001 | Richmond et al. | |
| 6,269,270 B1 | 7/2001 | Boveja | |
| 6,304,775 B1 | 10/2001 | Iasemidis et al. | |
| 6,324,421 B1 | 11/2001 | Stadler et al. | |
| 6,337,997 B1 | 1/2002 | Rise | |
| 6,339,725 B1 | 1/2002 | Naritoku et al. | |
| 6,341,236 B1 | 1/2002 | Osorio et al. | |
| 6,356,788 B2 | 3/2002 | Boveja | |
| 6,366,814 B1 | 4/2002 | Boveja et al. | |
| 6,459,936 B2 | 10/2002 | Fischell et al. | |
| 6,473,639 B1 | 10/2002 | Fischell et al. | |
| 6,473,644 B1 | 10/2002 | Terry et al. | |
| 6,484,132 B1 | 11/2002 | Hively et al. | |
| 6,505,074 B2 | 1/2003 | Boveja et al. | |
| 6,549,804 B1 | 4/2003 | Osorio et al. | |
| 6,556,868 B2 | 4/2003 | Naritoku et al. | |
| 6,564,102 B1 | 5/2003 | Boveja | |
| 6,587,719 B1 | 7/2003 | Barrett et al. | |
| 6,587,727 B2 | 7/2003 | Osorio et al. | |
| 6,600,956 B2 | 7/2003 | Maschino et al. | |
| 6,606,523 B1 | 8/2003 | Jenkins | |
| 6,609,025 B2 | 8/2003 | Barrett et al. | |
| 6,610,713 B2 | 8/2003 | Tracey | |
| 6,611,715 B1 | 8/2003 | Boveja | |
| 6,615,085 B1 | 8/2003 | Boveja | |
| 6,615,081 B1 | 9/2003 | Boveja | |
| 6,622,038 B2 | 9/2003 | Barrett et al. | |
| 6,622,041 B2 | 9/2003 | Terry, Jr. et al. | |
| 6,622,047 B2 | 9/2003 | Barrett et al. | |
| 6,658,294 B1 | 12/2003 | Zadeh et al. | |
| 6,662,052 B1 | 12/2003 | Sarwal et al. | |
| 6,668,191 B1 | 12/2003 | Bogeja | |
| 6,671,555 B2 | 12/2003 | Gielen et al. | |
| 6,671,556 B2 | 12/2003 | Osorio et al. | |
| 6,681,003 B2 | 1/2004 | Linder et al. | |
| 6,684,104 B2 | 1/2004 | Gordon et al. | |
| 6,684,105 B2 | 1/2004 | Cohen et al. | |
| 6,708,064 B2 | 3/2004 | Rezai | |
| 6,721,603 B2 | 4/2004 | Zabara et al. | |
| 6,760,626 B1 | 7/2004 | Boveja | |
| 6,764,498 B2 | 7/2004 | Mische | |
| 6,768,969 B1 | 7/2004 | Nikitin et al. | |
| 6,819,956 B2 | 11/2004 | Dilorenzo | |
| 6,904,390 B2 | 6/2005 | Nikitin et al. | |
| 6,920,357 B2 | 7/2005 | Osorio et al. | |
| 6,922,592 B2 | 7/2005 | Thompson et al. | |
| 6,934,580 B1 | 8/2005 | Osorio et al. | |
| 6,944,501 B1 | 9/2005 | Pless | |
| 6,959,215 B2 | 10/2005 | Gliner et al. | |
| 6,961,618 B2 | 11/2005 | Osorio et al. | |
| 7,006,872 B2 | 2/2006 | Gielen et al. | |
| 7,043,305 B2 | 5/2006 | Kenknight et al. | |
| 7,050,856 B2 | 5/2006 | Stypulkowski | |
| 7,054,792 B2 | 5/2006 | Frei et al. | |
| 7,076,288 B2 | 7/2006 | Skinner | |
| 7,079,977 B2 | 7/2006 | Osorio et al. | |
| 7,134,996 B2 | 11/2006 | Bardy | |
| 7,146,211 B2 | 12/2006 | Frei et al. | |
| 7,149,572 B2 | 12/2006 | Frei et al. | |
| 7,149,581 B2 | 12/2006 | Goedeke | |
| 7,156,808 B2 | 1/2007 | Quy | |
| 7,156,809 B2 | 1/2007 | Quy | |
| 7,164,941 B2 | 1/2007 | Misczynski et al. | |
| 7,167,743 B2 | 1/2007 | Heruth et al. | |
| 7,167,750 B2 | 1/2007 | Knudson et al. | |
| 7,171,271 B2 | 1/2007 | Koh et al. | |
| 7,188,053 B2 | 3/2007 | Nikitin et al. | |
| 7,228,167 B2 | 6/2007 | Kara et al. | |
| 7,231,254 B2 | 6/2007 | Dilorenzo | |
| 7,236,831 B2 | 6/2007 | Firlik et al. | |
| 7,242,983 B2 | 7/2007 | Frei et al. | |
| 7,254,439 B2 | 8/2007 | Misczynski et al. | |
| 7,263,467 B2 | 8/2007 | Sackellares et al. | |
| 7,265,676 B2 | 9/2007 | Gordon et al. | |
| 7,277,758 B2 | 10/2007 | Dilorenzo | |
| 7,280,867 B2 | 10/2007 | Frei et al. | |
| 7,282,030 B2 | 10/2007 | Frei et al. | |
| 7,292,890 B2 | 11/2007 | Whitehurst et al. | |
| 7,295,881 B2 | 11/2007 | Cohen et al. | |
| 7,305,268 B2 | 12/2007 | Gliner et al. | |
| 7,321,837 B2 | 1/2008 | Osorio et al. | |
| 7,324,850 B2 | 1/2008 | Persen et al. | |
| 7,324,851 B1 | 1/2008 | Dilorenzo | |
| 7,340,302 B1 | 3/2008 | Falkenberg et al. | |
| 7,353,064 B2 | 4/2008 | Gliner et al. | |
| 7,366,572 B2 | 4/2008 | Heruth et al. | |
| 7,373,199 B2 | 5/2008 | Sackellares et al. | |
| 7,389,144 B1 | 6/2008 | Osorio et al. | |
| 7,401,008 B2 | 7/2008 | Frei et al. | |
| 7,403,820 B2 | 7/2008 | Dilorenzo | |

(56) References Cited

U.S. PATENT DOCUMENTS

| | | |
|---|---|---|
| 7,483,747 B2 | 1/2009 | Gliner et al. |
| 7,894,890 B2 | 2/2011 | Sun et al. |
| 2002/0072782 A1 | 6/2002 | Osorio et al. |
| 2002/0099417 A1 | 7/2002 | Naritoku et al. |
| 2002/0151939 A1 | 10/2002 | Rezai |
| 2002/0188214 A1 | 12/2002 | Misczynski et al. |
| 2004/0122484 A1 | 6/2004 | Hatlestad et al. |
| 2004/0122485 A1 | 6/2004 | Stahmann et al. |
| 2004/0133119 A1 | 7/2004 | Osorio et al. |
| 2004/0138647 A1 | 7/2004 | Osorio et al. |
| 2004/0138711 A1 | 7/2004 | Osorio et al. |
| 2004/0158119 A1 | 8/2004 | Osorio et al. |
| 2004/0199212 A1 | 10/2004 | Fischell et al. |
| 2005/0124901 A1 | 6/2005 | Misczynski et al. |
| 2005/0143786 A1 | 6/2005 | Boveja |
| 2005/0148893 A1 | 7/2005 | Misczynski et al. |
| 2005/0148895 A1 | 7/2005 | Misczynski et al. |
| 2005/0154425 A1 | 7/2005 | Boveja et al. |
| 2005/0177192 A1 | 8/2005 | Rezai et al. |
| 2005/0187590 A1 | 8/2005 | Boveja et al. |
| 2005/0187796 A1 | 8/2005 | Rosenfeld et al. |
| 2005/0192644 A1 | 9/2005 | Boveja et al. |
| 2005/0197590 A1 | 9/2005 | Osorio et al. |
| 2005/0277998 A1 | 12/2005 | Tracey et al. |
| 2006/0009815 A1 | 1/2006 | Boveja et al. |
| 2006/0155495 A1 | 7/2006 | Osorio et al. |
| 2006/0167497 A1 | 7/2006 | Armstrong et al. |
| 2006/0173493 A1 | 8/2006 | Armstrong et al. |
| 2006/0224191 A1 | 10/2006 | Dilorenzo |
| 2006/0241697 A1 | 10/2006 | Libbus et al. |
| 2006/0241725 A1 | 10/2006 | Libbus et al. |
| 2006/0293720 A1 | 12/2006 | Dilorenzo |
| 2007/0027486 A1 | 2/2007 | Armstrong |
| 2007/0072425 A1 | 3/2007 | Kikui et al. |
| 2007/0088404 A1 | 4/2007 | Wyler et al. |
| 2007/0100278 A1 | 5/2007 | Frei et al. |
| 2007/0100392 A1 | 5/2007 | Maschino et al. |
| 2007/0123758 A1 | 5/2007 | Miesel et al. |
| 2007/0208212 A1 | 9/2007 | Dilorenzo |
| 2007/0213785 A1 | 9/2007 | Osorio et al. |
| 2007/0233192 A1 | 10/2007 | Craig et al. |
| 2007/0239210 A1 | 10/2007 | Libbus et al. |
| 2007/0244407 A1 | 10/2007 | Osorio |
| 2007/0282177 A1 | 12/2007 | Pilz |
| 2008/0033508 A1 | 2/2008 | Frei et al. |
| 2008/0064934 A1 | 3/2008 | Frei et al. |
| 2008/0071327 A1 | 3/2008 | Miesel et al. |
| 2008/0081941 A1 | 4/2008 | Tononi |
| 2008/0103548 A1 | 5/2008 | Fowler et al. |
| 2008/0119900 A1 | 5/2008 | Dilorenzo |
| 2008/0195166 A1 | 8/2008 | Sun et al. |
| 2008/0208285 A1 | 8/2008 | Fowler et al. |
| 2008/0234598 A1 | 9/2008 | Snyder et al. |
| 2008/0234785 A1 | 9/2008 | Nakayama et al. |
| 2008/0269631 A1 | 10/2008 | Denison et al. |
| 2008/0319281 A1* | 12/2008 | Aarts ............ A61B 5/02438 600/301 |
| 2009/0198145 A1 | 8/2009 | Chow |
| 2010/0087701 A1 | 4/2010 | Berka et al. |
| 2011/0029044 A1 | 2/2011 | Hyde et al. |
| 2011/0112381 A1 | 5/2011 | Sun et al. |
| 2011/0270096 A1* | 11/2011 | Osorio ............ A61B 5/02405 600/483 |
| 2011/0270346 A1 | 11/2011 | Frei et al. |
| 2011/0295083 A1 | 12/2011 | Doelling et al. |
| 2012/0116183 A1 | 5/2012 | Osorio |
| 2012/0277605 A1 | 11/2012 | Colborn |
| 2012/0277618 A1 | 11/2012 | Giftakis et al. |
| 2013/0056099 A1 | 3/2013 | Alkemade et al. |
| 2014/0364770 A1* | 12/2014 | Slonneger ............ A61B 5/4812 600/595 |

OTHER PUBLICATIONS

Chakravarthy, N. et al., "Controlling Synchronization in a Neuron-Level Population Model," International Journal of Neural Systems, vol. 17, No. 2, 2007, pp. 123-138.

Chen, C. et al., "Vagal Efferent Fiber Stimulation Ameliorates Pulmonary Microvascular Endothelial Cell Injury by Downregulating Inflammatory Responses," Inflammation, vol. 36, No. 6, Dec. 2013, pp. 1567-1575.

Dodrill, C.B. et al., "Effects of Vagal Nerve Stimulation on Cognition and Quality of Life in Epilepsy," Epilepsy & Behavior, vol. 2, Issue 1, 2001, pp. 46-53.

Frei, M.G. et al., "Left Vagus Nerve Stimulation with the Neurocybernetic Prosthesis Has Complex Effects on Heart Rate and on its Variability in Humans," Epilepsia, vol. 42, No. 8, 2001, pp. 1007-1016.

Iasemidis, L.D. et al., "Spatiotemporal Transition to Epileptic Seizures: A Nonlinear Dynamical Analysis of Scalp and Intracranial EEG Recordings," Spatiotemporal Models in Biological and Artificial Systems, IOS Press, 1997, pp. 81-88.

International Application No. PCT/us2015/024879, PCT Search Report and Written Opinion dated Jun. 25, 2015, 13 pages.

International Application No. PCT/US2015/024960, "PCT Search Report and Written Opinion", dated Jun. 17, 2015, Rijswijk and Munich.

International Search Report for PCT Patent Application No. PCT/US2015/024879, dated Jun. 25, 2015, 5 pages.

Jaseja, H., "Vagal Nerve Stimulation Technique: Enhancing its Efficacy and Acceptability by Augmentation with Auto Activation and Deactivation Mode of Operation," Medical Hypotheses, vol. 63, Issue 1, 2004, pp. 76-79.

Kucera, M., "'Active Air' Inhalation Therapy: Autonomic Regulation Mechanisms with Use of Heart Rate Variability Analysis," Explore! vol. 16, No. 2, 2007, 3 pages.

Malow, B.A. et al., "Vagus Nerve Stimulation Reduces Daytime Sleepiness in Epilepsy Patients," Neurology, vol. 57, Issue 5, 2001, pp. 879-884.

Valdes-Cruz, A. et al., "Chronic Stimulation of the Cat Vagus Nerve Effect on Sleep and Behavior," Progress in Neuro-Psychopharmacology & Biological Psychiatry, vol. 26, Issue 1, 2002, pp. 113-118.

Zabara, J., "Neuroinhibition in the Regulation of Emesis," Space Life Sciences, vol. 3, Issue 3, 1972, pp. 282-292.

* cited by examiner

Reference Background Heart Rate
$(BG_R = 0.95*BG_{n-1} + 0.05*FG_n)$

Foreground Heart Rate

Modified Background Heart Rate
$(BG_M = \lambda*BG_{n-1} + (1-\lambda)*FG_n)$

DETECTING SEIZURES BASED ON HEARTBEAT DATA

CROSS-REFERENCE RELATED APPLICATION

This application is a continuation of U.S. patent application Ser. No. 14/262,449, filed Apr. 25, 2014, which is related to U.S. patent application Ser. No. 14/262,508, filed Apr. 25, 2014, both of which are hereby incorporated by reference herein in their entireties.

FIELD OF THE DISCLOSURE

The present disclosure is generally related to detecting seizures based on heartbeat data.

BACKGROUND

Advances in technology have led to the development of medical devices that can be implanted within a living organism, such as a human, to provide treatment or monitoring. For example, a medical device may detect when a seizure occurs in a patient. Early detection of a seizure may allow appropriate responsive action to be taken. Such actions may include sending an alert signal to the patient or a caregiver, initiating a treatment therapy, or taking remedial action such as making the patient and/or an environment around the patient safe. One way to detect seizures is by monitoring a heartbeat of the patient to determine whether the heartbeat increases beyond a threshold. However, other factors can also cause the heartbeat to increase beyond the threshold. Thus, seizure detection based on a heartbeat may be subject to a significant number of false positives.

SUMMARY

A medical device monitoring and/or providing therapy to a patient may detect and respond to seizures based on patient heartbeat data and based on patient activity data (including patient state data). The medical device may use a seizure detection algorithm that is capable of distinguishing between pathological changes in the detected heartbeat, which may indicate a seizure, and non-pathological changes in the detected heartbeat. The non-pathological changes may correspond to normal physiological functioning as opposed to a seizure. The non-pathological changes may be difficult to distinguish from the pathological changes based solely on information associated with the heartbeat.

For example, the patient's heartbeat may increase when a seizure event occurs (e.g., a pathological change). However, the patient's heartbeat may also change when the patient engages in a state of physical activity (such as running, jumping, exercising, swimming, etc.) or the patient assumes a state or changes to or from a state (such as initiating running, awaking from sleep, going to sleep, changing from healthy to sick, etc.). Other external factors may also cause the patient's heartbeat to increase. For example, a change in temperature may contribute to an increase in the patient's heartbeat. It may become difficult for the medical device to determine whether an increase in the patient's heartbeat is due to a seizure, physical activity, or other external factors.

To address such concerns, the medical device may account for the physical activity and/or other external factors when determining whether or not a seizure event is indicated by heartbeat data. For example, the medical device may use an algorithm that detects whether or not a seizure event is present based on a background heart rate and a foreground heart rate. The foreground heart rate may correspond to a rate at which the patient's heart is beating at a present time, which can be the most-recent heart rate value obtained from the patient or be an average of several recent heart rate values that are adjacent to and include the most-recent heart rate value. The background heart rate may be a function of the foreground heart rate and a previously-determined background heart rate. For example, the algorithm may be expressed as $BG_n = \lambda * BG_{n-1} + (1-\lambda) * FG_n$, where $BG_n$ is the background heart rate at the present time (n), $BG_{n-1}$ is the previously-determined background heart rate, $FG_n$ is the foreground heart rate at the present time (n), and $\lambda$ is a weighting factor. The previously-determined background heart rate may correspond to an average heart rate during a moving period of time or time window (e.g., an average heart rate during a moving five minute time window that remains immediately prior to the present time), with the period of time or time window being selected to capture a sufficient number of stable heart beats to provide an average heart rate value that is representative of the patient's heart rate and not heavily influenced by any extremely-high or low single heart beat or grouping of heart beats. When a ratio of the foreground heart rate and the background heart rate at the present time exceeds a seizure detection threshold, the medical device may determine that a seizure event is present.

A value of the weighting factor may be based on physical activity and/or other external factors that affect heart rate. The weighting factor may be zero, one, or between zero and one. As can be appreciated, when the weighting factor is set at a high value that is at or close to one, the calculation of the background heart rate will be heavily influenced by the value of the previously determined-background heart rate, thus providing a background heart rate that is greatly dependent on a window of time corresponding to the time period assigned when determining the previously-determined heart rate. As can also be appreciated, when the weighting factor is set at a low value that is at or close to zero, the calculation of the background heart rate will be heavily influenced by the value of the foreground heart rate, thus providing a background heart rate that is greatly dependent on an instant heart rate or recently-measured heart rate values. As can be further appreciated, when the weighting factor is set at a middle value that is at or close to 0.5, the calculation of the background heart rate will be equally influenced by the values of the previously-determined heart rate and the foreground heart rate, thus providing a background heart rate that is balanced in its dependence on previously-measured heart rate values and recently-measured heart rate values. As an illustrative non-limiting example, the value of the weighting factor may be approximately equal to 0.95 when the patient is in an idle state (e.g., sleep), which would provide a background heart rate that heavily depends (e.g., 95% dependence) on the previously-determined background heart rate and lightly depends (e.g., 5% dependence) on the foreground heart rate. When the patient is undergoing physical activity such as running on a treadmill, or the patient is subject to external factors that affect heart rate, the value of the weighting factor may be set to a lesser value than with the idle state, which will generate a background heart rate that is more dependent on the foreground heart rate than the previously-determined background heart rate, and/or generate a background heart rate that is based on a balancing of the foreground heart rate and the previously-determined heart rate. For example, when the value of the weighting factor is reduced from 0.95 to 0.50 when the patient leaves an idle state to undergo a particular physical activity, the background heart rate can be 50% dependent on the previously-determined background heart rate and 50% dependent on the foreground heart rate, thereby providing a background heart rate that accounts for a recent change in the heart rate due to the physical activity and accounts for the more-stable and longer-measured heart rate that was observed before the recent change in heart rate.

Thus, physical activity and/or external factors may be used alone or in combination to determine the background heart rate by changing the value of the weighting factor based on the physical activity and/or external factors that affect heart rate. As a result, when the background heart rate is compared to the foreground heart rate to determine whether a seizure event is occurring, physical activity and/or external factors are taken into account.

In a particular embodiment, a method includes receiving heartbeat data of a patient and receiving activity data of the patient. The activity data can provide one or more activity values that are related to an activity level of the patient and that are independent of the heartbeat data. The method further includes determining a value of a weighting factor based on the activity data. The method also includes determining modified heartbeat data by applying the weighting factor to at least a portion of the heartbeat data. The method also includes detecting a seizure event based on the modified heartbeat data.

In another particular embodiment, a medical device includes a first interface to receive heartbeat data of a patient and a second interface to receive activity data of the patient. The activity data includes one or more activity values that are related to an activity level of the patient and that are measured independently of the heartbeat data. The medical device also includes a processor to determine a value of weighting factor based on the activity data. The processor determines modified heartbeat data by applying the weighting factor to at least a portion of the heartbeat data. The processor also detects a seizure event based on the modified heartbeat data.

In another particular embodiment, a non-transitory computer readable medium stores instructions that are executable be a processor to cause the processor perform operations. The operations include receiving heartbeat data of a patient and receiving activity data of the patient. The activity data includes one or more activity values that are related to an activity level of the patient and that are measured independently of the heartbeat data. The operations further include determining a value of a weighting factor based on the activity data and determining modified heartbeat data by applying the weighting factor to at least a portion of the heartbeat data. The operations also include detecting a seizure event based on the modified heartbeat data.

The features, functions, and advantages that have been described can be achieved independently in various embodiments or may be combined in yet other embodiments, further details of which are disclosed with reference to the following description and drawings.

DETAILED DESCRIPTION

Figure 1:
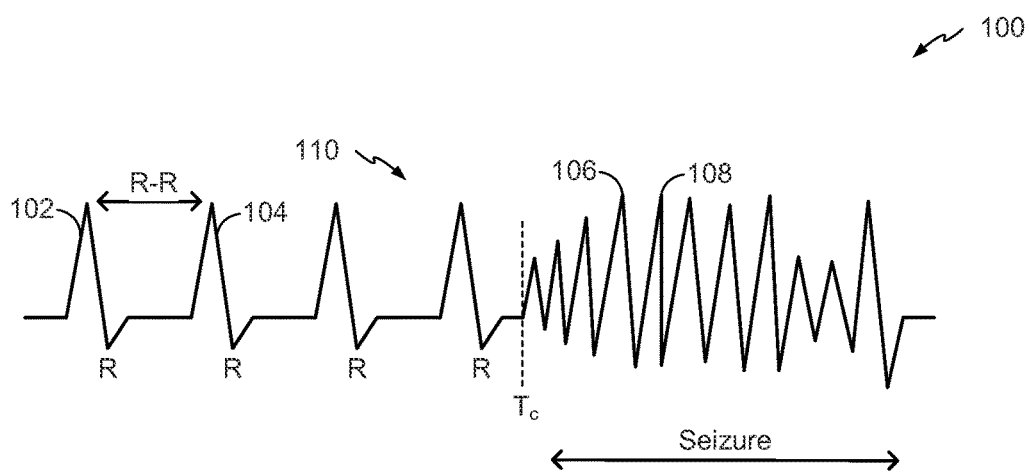
FIG. 1 is a particular illustrative embodiment of a diagram illustrating heartbeat data modification based on activity data.
Figure 1:
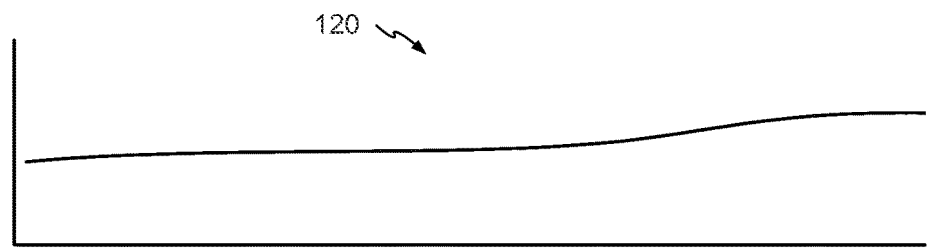
Figure 1:
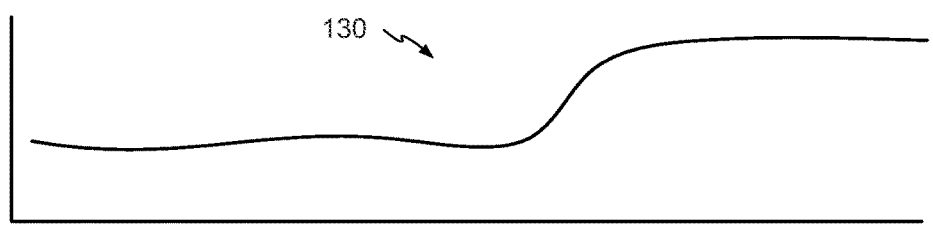
Figure 1:
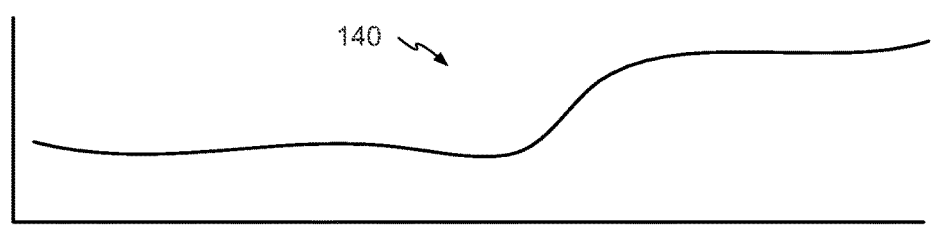

FIG. 1 is a particular illustrative embodiment of a diagram 100 illustrating heartbeat data modification based on physical activity. The diagram 100 includes a first trace 110 illustrating an electrocardiogram of a patient, a second trace 120 illustrating a background heart rate of the patient which is derived from the first trace 110 and calculated using a fixed weighting factor, a third trace 130 illustrating a foreground heart rate of the patient which is derived from the first trace 110, and a fourth trace 140 illustrating a modified background heart rate of the patient which is derived from the first trace 110 and calculated using a weighting factor and adjusted based on activity data. The four traces 110, 120, 130, and 140 of diagram 100 are aligned with each other to provide identical x-axis representation of time and to provide similar y-axis representations of magnitude of the measured or calculated parameter.

The electrocardiogram illustrated in the first trace 110 may include a plurality of R waves. For example, the electrocardiogram may include a first R wave 102 and a second R wave 104. A time between respective points on the first R wave 102 and the second R wave 104 is an R-R interval. The first R wave 102 and the second R wave 104 may correspond to a first and second heartbeat, respectively, and the R-R interval may correspond to an amount of time that elapses between consecutive heartbeats (e.g., a heartbeat rate, also referred to as a "heart rate").

A faster heartbeat may result in a shorter R-R interval between consecutive heartbeats (e.g., R waves). For example, a third R wave 106 and a fourth wave 108 may have a shorter R-R interval than the R-R interval between the first and second R waves 102, 104. Thus, the patient's heart is beating at a faster rate at a time corresponding to the third and fourth R waves 106, 108 as opposed to a time corresponding to the first and second R waves 102, 104. As illustrated by the first trace 110, an increased rate of the patient's heartbeat (e.g., shorter R-R intervals) may be indicative of a seizure event. For example, the seizure event may begin at a critical time (Tc) when the rate of the patient's heartbeat exceeds a threshold level.

The background heart rate of the patient illustrated in the second trace 120 may be expressed as $BG_R = 0.95 * BG_{n-1} + 0.05 * FG_n$, where $BG_R$ is a reference background heart rate at the present time (n), $BG_{n-1}$ is the previously-determined background heart rate, and FGn is the foreground heart rate at the present time (n). The previously-determined background heart rate may be generated by taking an electrocardiogram over a particular time span and performing an infinite impulse response (IIR) operation on the electrocardiogram. For example, the previously-determined background heart rate may correspond to an IIR operation on an electrocardiogram spanning a five minute time period before the present time (n). In another example, the previously-determined background heart rate may correspond to an IIR operation on an electrocardiogram spanning a time period determined by a number of heart beats before the present time (n).

The foreground heart rate ($FG_n$) at the present time (n) is illustrated in the third trace 130. The foreground heart rate may be generated by taking an electrocardiogram over a time span corresponding to a most recent R-R interval. For example, the foreground heart rate may correspond to a current heart rate. When the current heart rate increases, a magnitude of the foreground heart rate increases. When the current heart rate decreases, the magnitude of the foreground heart rate decreases.

Referring back to the exemplary embodiment represented with second trace 120, ninety-five percent of the reference background heart rate is based on a heart rate spanning over a previous five minute period (e.g., the previously-determined background heart rate) and five percent of the reference background heart rate is based on the foreground heart rate illustrated in the third trace 130. Thus, when determining the reference background heart rate, the previously-determined background heart rate is weighted at a fixed rate (e.g., 0.95) and the foreground heart rate is weighted at a fixed rate (e.g., 0.05). When comparing the foreground heart rate illustrated in the third trace 130 to the reference background heart rate illustrated in the second trace 120, a ratio of the foreground heart rate and the reference background heart rate may be calculated, and the ratio may be compared to a seizure threshold and, when the threshold is exceeded, detect the occurrence of a seizure event at the critical time ($T_c$).

However, if the increased heart rate at the critical time ($T_c$) is associated with a physical activity of the patient as opposed to a seizure, then using the reference background heart rate in the second trace 120 may result in a false detection of a seizure event. For example, volitional motion or other non-seizure activity may increase heart rate, and the dominance of the previously-determined background heart rate (when, e.g., weighted at 95%) in the calculation of the reference background heart rate and/or the ratio may result in a false indication of a seizure event. To reduce the likelihood of detecting a false seizure event, the modified background heart rate illustrated in the fourth trace 140 may be used along with the foreground heart rate illustrated in the third trace 130 to detect whether a seizure event is present.

For example, the modified background heart rate may factor in an activity level of the patient to account for the increased heart rate. The modified background heart rate may be expressed as $BG_M = \lambda * BG_{n-1} + (1-\lambda) * FG_n$, where $BG_M$ is the modified background heart rate at the present time (n), $BG_{n-1}$ is the previously-determined background heart rate, $FG_n$ is the foreground heart rate at the present time (n), and $\lambda$ is a weighting factor.

A value of the weighting factor may be based on activity data. In a particular embodiment, the activity data includes accelerometer data, body temperature data, electromyography data, respiration data, perspiration data, impedance data, or a combination thereof. The activity data may include data obtained from an electroencephalography (EEG) sensor, an electrooculography (EOG) sensor, an electrocardiography (ECG) sensor, an electromyography (EMG) sensor, an accelerometer, or a combination thereof, as disclosed in contemporaneously-filed U.S. patent application Ser. No. 14/262,508, entitled "Cranial Nerve Stimulation To Treat Depression During Sleep," which is hereby incorporated by reference as though fully set forth herein. In another particular embodiment, the activity data may correspond to one or more activity values that are related to an activity level of the patient. The activity values may be measured independently of the heart rate of the patient (e.g., measured independently of heartbeat data). The activity values may also be based on a state of the patient or a change of patient state, e.g., based on an activity state, a sleep state, or a change in the patient activity or sleep state. The activity values may also be related to measurements corresponding patient temperature, patient muscle activity, breathing rate, a skin response such as sweating, or combinations thereof. For example, activity data measured with an accelerometer may have a first activity value associated with running, activity data measured with a respiration sensor may have a second activity value associated with walking, activity data measured with an EEG sensor may have a third activity value associated with sleeping, etc. With regard to sleeping, the activity value may correspond to a sleep state of the patient so as to increase or decrease the weighting factor when the patient is in a sleep state that, for example, exhibits reduced or increased body movements, when the patient transitions from one sleep state to another sleep state, when the patient moves or changes positions during sleep, and/or when the patient awakes from sleep, as disclosed in contemporaneously-filed U.S. patent application Ser. No. 14/262,508, entitled "Cranial Nerve Stimulation To Treat Depression During Sleep," which is hereby incorporated by reference as though fully set forth herein. The value of the weighting factor may decrease as an activity level of the patient increases. As a non-limiting example, the value of the weighting factor may be approximately 0.95 when the activity corresponds to sleeping or to a sleep state, 0.75 when the activity corresponds to walking, and 0.50 when the activity corresponds to running. As the weighting factor decreases, the modified background heart rate becomes more dependent on the foreground heart rate (e.g., more dependent on a current heart rate of the patient) and less dependent on the previously-determined background heart rate. Thus, the modified background heart rate updates more quickly than the reference background heart rate when the patient is engages in activities that cause an immediate or foreseeable increase in heart rate.

The modified background heart rate may become increasingly similar to the foreground heart rate as the value of the weighting factor decreases. For example, the third trace 130 (e.g., the foreground heart rate) may become increasingly similar to the fourth trace 140 (e.g., the modified background heart rate) as the value of the weighting factor approaches zero. As a result, when comparing the foreground heart rate illustrated in the third trace 130 to the modified background heart rate illustrated in the fourth trace 140, a ratio of the foreground heart rate and the modified background heart rate may not exceed the seizure threshold at the critical time ($T_c$) when the increased heart rate is based on patient activity. Thus, using the modified background heart rate to detect a seizure event may yield fewer false positives.

Figure 2:
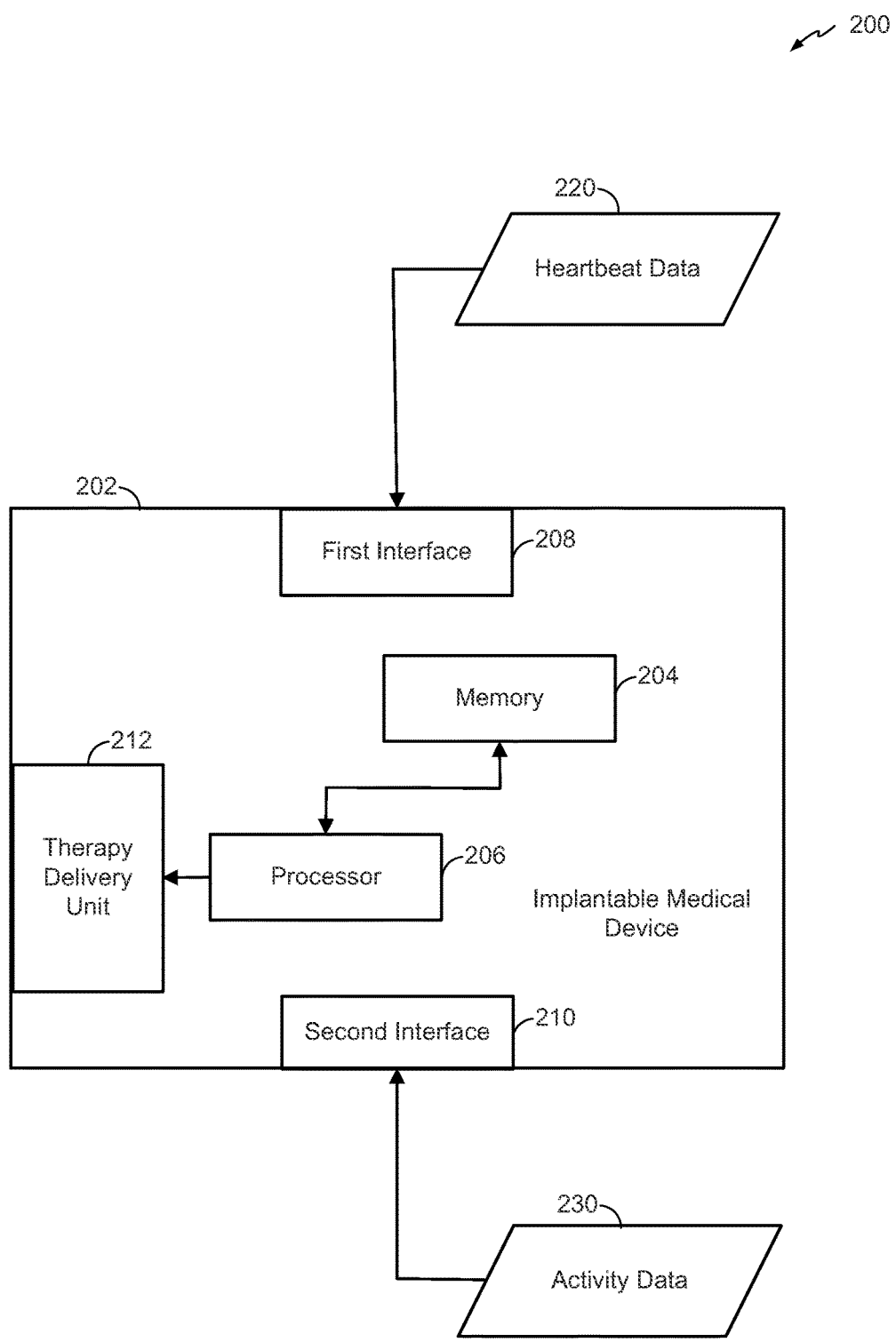
FIG. 2 is a particular embodiment of a system that is operable to detect a seizure event based on heartbeat data and activity data.

Referring to FIG. 2, a system 200 that is operable to detect a seizure event based on heartbeat data and activity data is shown. The system 200 includes a patient-contacting medical device 202, which can be, for example, an implantable medical device or an external device fixed to the surface of a patient's skin. The medical device 202 includes a processor 206 that is coupled to a memory 204 and can also be coupled directly or wirelessly to a therapy delivery unit 212, which may be part of the medical device 202 (as illustrated in FIG. 2) or located external to the medical device 202.

The medical device 202 includes a first interface 208 that is coupled to receive heartbeat data 220 of a patient. The heartbeat data 220 may be generated from an electrode implanted within, or externally coupled to, the patient. The heartbeat data 220 of the patient may include electrocardiogram data. For example, the heartbeat data 220 may correspond to the electrocardiogram illustrated in the first trace 110 of FIG. 1. In a particular embodiment, the heartbeat data 220 is a numeric value indicating a most recent R-R interval or a signal corresponding to an electrocardiogram data trace. The first interface 208 may be configured to provide the heartbeat data 220 to the processor 206.

The medical device also includes a second interface 210 that is coupled to receive activity data 230 of the patient. The activity data 230 may be generated from a component (such as an accelerometer) within the medical device 202 (not shown in FIG. 2) or an external device such as an electrode implanted within, or externally coupled to, the patient as illustrated in FIG. 2. In a particular embodiment, the activity data 230 includes accelerometer data, body temperature data, electromyography data, perspiration data, impedance data, or a combination thereof. The activity data 230 may include one or more activity values that are related to an activity level of the patient. For example, a first activity value may be associated with running, a second activity value may be associated with walking, a third activity value may be associated with sleeping, etc. The activity values may be measured independently of the heartbeat data 220. In a particular embodiment, the activity data is a numeric value or signal indicating a measurement that is associated with the activity level of the patient. The second interface 210 may be configured to provide the activity data 230 to the processor 206.

The processor 206 may be configured to receive the heartbeat data 220 from the first interface 208 and to receive the activity data 230 from the second interface 210. The processor 206 may perform an IIR operation on the heartbeat data 220 (e.g., perform an IIR operation on the electrocardiogram data) to generate a background heart rate for spanning over a time period (e.g., a five minute time period). The processor 206 may also be configured to determine a value of a weighting factor based on the activity data 230.

The processor 206 may further be configured to determine modified heartbeat data by applying the weighting factor to at least a portion of the heartbeat data. Determining the modified heartbeat data may include determining a background heart rate based on a previously-determined background heart rate, a most recent R-R interval, and the weighting factor. Determining the modified heartbeat data may also include determining a foreground heart rate based on a most recent R-R interval. For example, the modified heartbeat data may correspond to the modified background heart rate illustrated in the fourth trace 140 of FIG. 1 and may be expressed as $BG_M = \lambda * BG_{n-1} + (1-\lambda) * FG_n$, where $BG_M$ is the modified heartbeat data (e.g., the modified background heart rate), $BG_{n-1}$ is a previously-determined background heart rate, FGn is a foreground heart rate at the present time (n), and $\lambda$ is the weighting factor determined based on the activity data 230. Thus, the modified heartbeat data may be determined as a sum of a first value and a second value. The first value ($\lambda * BG_{n-1}$) may be the weighting factor times the previously-determined background heart rate, and the second value ($(1-\lambda) * FG_n$) may be one minus the weighting factor times the most recent R-R interval (e.g., the foreground heart rate).

In response to the activity data 230 indicating an increased activity level of the patient, the processor 206 is configured to determine the value of the weighting factor such that an effect of prior heartbeat data ($BG_{n-1}$) on the modified heartbeat data is decreased. As a non-limiting example, the value of the weighting factor may be approximately 0.95 when the activity corresponds to sleeping or a sleep state, 0.75 when the activity corresponds to walking, and 0.50 when the activity corresponds to running. Thus, the value of the weighting factor decreases as the activity level of the patient increases. As can be appreciated, the calculation of modified background heart rate and the weighting factor can be modified to provide the same operation described above, but configured so that the value of the weighting factor increases as the activity level of the patient increases.

The processor 206 may also be configured to detect an indication of noise in the heartbeat data 220. Noise may be detected via patterns in an electrocardiogram, such as the electrocardiogram illustrated in the first trace 110 of FIG. 1. For example, noise may be present if the detected heartbeat falls below a lower threshold or rises above an upper threshold. In a particular embodiment, the lower threshold is about 35 beats per minute (bpm) and the upper threshold is about 180 bpm. As another example, noise may be present if a beat-to-beat variability rises above an upper threshold or falls below a lower threshold. In a particular embodiment, the upper threshold may be about 115 percent and the lower threshold is about 65 percent.

In response to the detected noise in the heartbeat data 220 increasing, the processor 206 may determine the value of the weighting factor such that an effect of prior heartbeat data ($BG_{n-1}$) on the modified heartbeat data is decreased. For example, in response to the detected noise in the heartbeat data 220 increasing, the processor 206 may lower the value of the weighting factor so that the modified heartbeat data is more dependent on the foreground heart rate. In response to the detected noise in the heartbeat data decreasing, the processor 206 may determine the value of the weighting factor such that the effect of the prior heartbeat data ($BG_{n-1}$) on the modified heartbeat data is increased. For example, in response to the detected noise in the heartbeat data 220 decreasing, the processor 206 may raise the value of the weighting factor so that the modified heartbeat data is more dependent on the previously-determined background heart rate The processor 206 may further be configured to detect a seizure event based on the modified heartbeat data. For example, the processor 206 may compare a ratio of the foreground heart rate and the modified background heart rate (e.g., the modified heartbeat data) to a seizure detection threshold. When the ratio exceeds the seizure detection threshold, the processor 206 may determine that a seizure event is present. When the ratio is below the seizure detection threshold, the processor 206 may determine that no seizure event is present. As explained with respect to FIG. 3, in response to detecting the seizure event, the processor 206 may be configured, for example, to provide a notification that a seizure is detected, to initiate a recording of the seizure event, and/or to cause the therapy delivery unit 212 to apply stimulation to tissue of the patient.

The memory 204 may include tangible, non-transitory, computer-readable media (e.g., one or more computer memory devices). The processor 206 may be implemented using a single-chip processor or using multiple processors. The memory 204 may include various memory devices, such as registers, cache, volatile memory, and non-volatile memory. For example, the memory 204 can include cache that is accessible by the processor 206 to rapidly retrieve and store data. As a non-limiting example, the memory 204 may store information corresponding to the previously-determined background heart rate ($BG_{n-1}$) and/or weighting factor values for different activities. In a particular embodiment, a look-up table, an algorithm, or a combination thereof, is stored in the memory 204 to determine the weighting factor values based on the activity data 230, the detected noise in the heartbeat data 220, or a combination thereof. Examples of computer-readable media that the memory 204 may use include, but are not limited to: magnetic media such as hard disks, floppy disks, and magnetic tape; optical media such as CD-ROM disks; magneto-optical media; and specially configured hardware devices such as application-specific integrated circuits (ASICs), programmable logic devices (PLDs), and ROM and RAM devices.

The memory 204 may also store instructions that are executable by the processor 206 to implement various functions. To illustrate, the instructions may be executable by the processor 206 to cause the processor to perform operations including receiving the heartbeat data 220 and receiving the activity data 230. The operations may also include determining the value of the weighting factor based on the activity data 230 and determining modified heartbeat data by applying the weighting factor to at least a portion of the heartbeat data 220. The instructions may also be executable by the processor 206 to cause the processor to detect the seizure event based on the modified heartbeat data. In a particular embodiment, the instructions are executable by the processor 206 to detect R waves in an electrocardiogram, R-R intervals in an electrocardiogram, noise in the heartbeat data 220, other information descriptive of a heartbeat, or a combination thereof.

Additionally or in the alternative, the medical device 202 may include dedicated hardware implementations, such as application specific integrated circuits, programmable logic arrays and other hardware devices, to implement one or more functions of the processor 206. Accordingly, the present disclosure encompasses software, firmware, and hardware implementations.

When the heartbeat data 220 is received as an electrocardiogram trace, the processor 206, or an application-specific integrated circuit (ASIC), may perform an IIR operation on an electrocardiogram trace to detect R waves and R-R intervals. The processor 206 (or ASIC) may determine a foreground heart rate by monitoring the timing between the most recent R waves in the electrocardiogram. The processor 206 may also determine the modified background heart rate based on prior heartbeat data stored in the memory 204, the foreground heart rate, and the weighting factor. For example, the prior heartbeat data may be based on heartbeat data 220 received during a five minute window prior to the heartbeat data 220 associated with the foreground heart rate. Activity data 230 associated with patient may be provided to the processor 206 via the second interface 210 to determine the value of the weighting factor.

The processor 206 may detect whether a seizure event is present based on the heartbeat data 220 and the activity data 230. For example, the processor 206 may compare the ratio of the foreground heart rate and the modified background heart rate to the seizure detection threshold to determine whether the seizure event is present. In response to detecting the seizure event, the processor 206 may, for example, send a signal to provide a notification that a seizure is detected, to initiate a recording of the seizure event, and/or to the therapy delivery unit 212 to cause the therapy delivery unit 212 to stimulate a tissue of the patient.

Figure 3:
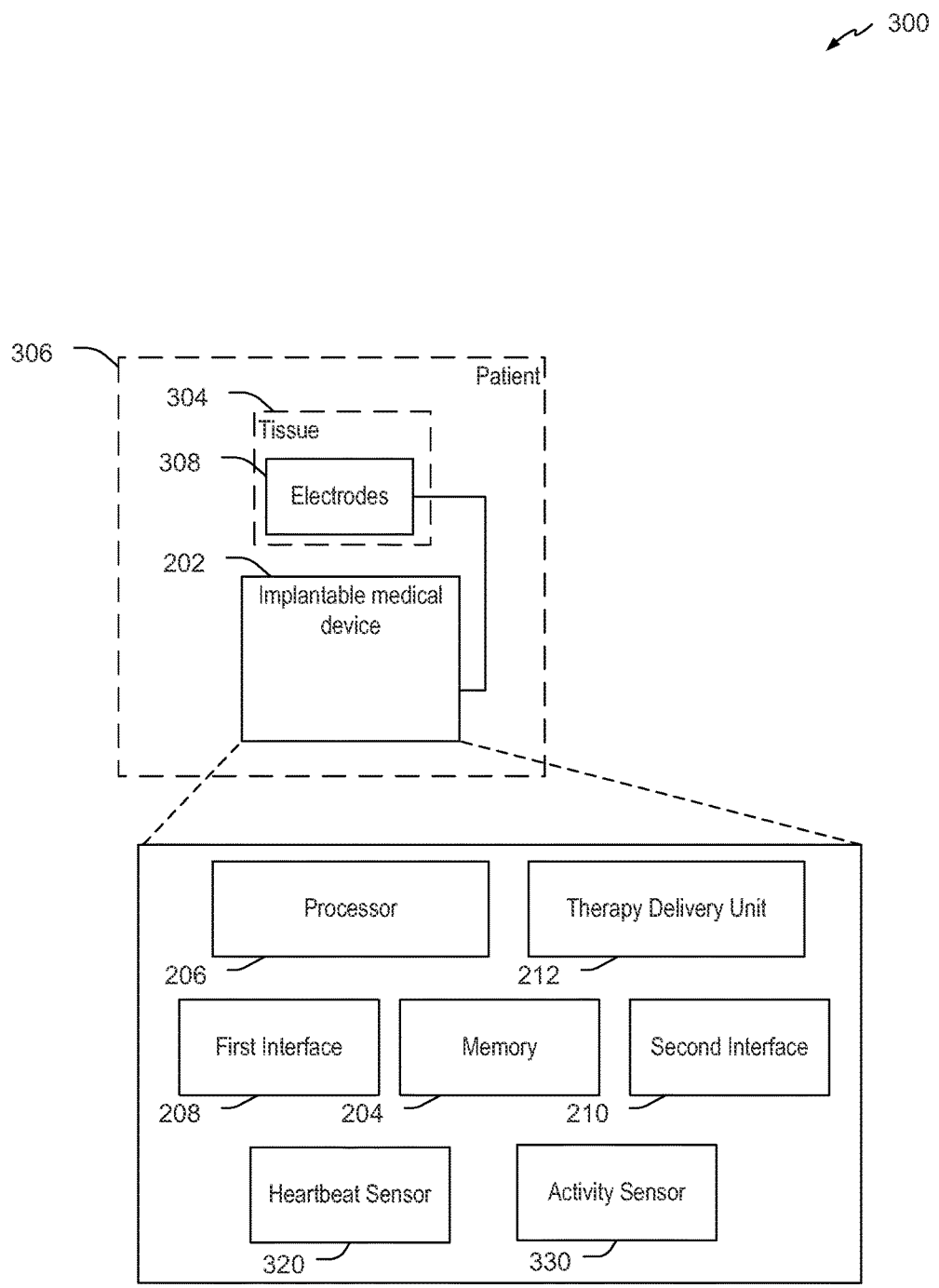
FIG. 3 is a block diagram of a particular embodiment of a medical device in communication with a patient that is operable to detect a seizure event based on heartbeat data and activity data.

Referring to FIG. 3, a block diagram of a particular embodiment of implantable medical device 202 within a patient is shown. The medical device 202 includes the memory 204, the processor 206, the first interface 208, the second interface 210, the therapy delivery unit 212, a heartbeat sensor 320, and an activity sensor 330.

The medical device 202 may be adapted to be surgically implanted in a patient 306 to detect a seizure event based on activity data 230 and heartbeat data 220, to provide therapy, to monitor one or more conditions, for another purpose, or any combination thereof. In a particular embodiment, the medical device 202 may be coupled to one or more electrodes 308 and may be adapted to deliver electrical stimulus to tissue 304 of the patient 306 via the electrodes 308. In a particular embodiment, the medical device 202 is an implantable nerve stimulation device. Examples of the implantable nerve stimulation device may include an implantable cranial nerve stimulation device, an implantable spinal cord stimulation device, etc. The electrodes 308 may be coupled to the medical device 202 and may be positioned proximate to or coupled to a nerve, such as a cranial nerve (e.g., the trigeminal nerve, the hypoglossal nerve, the vagus nerve or a branch of the vagus nerve).

The heartbeat sensor 320 may be configured to detect (e.g., sense) a heartbeat of the patient 306. For example, the heartbeat sensor 320 may be coupled to a nerve via the electrodes 308 to detect the heartbeat of the patient 306. In a particular embodiment, the heartbeat sensor 320 is an electrocardiogram (ESG) sensor. For example, based on the detected heartbeat, the heartbeat sensor 320 may generate electrocardiogram data and provide the electrocardiogram data to the processor 206. The electrocardiogram data may correspond to the electrocardiogram data illustrated by the first trace 110 of FIG. 1 and may indicate R waves and R-R intervals of the detected heartbeat. The activity sensor 330 may be configured to detect an activity level of the patient 306. For example, the activity sensor 330 may be coupled to a nerve via the electrodes 308 to detect an activity level of the patient 308. Alternatively, the activity sensor 330 may include a device that detects other indications of activity, such as an amount of perspiration, a body temperature, breathing rate, etc.

As explained with reference to FIG. 2, the medical device 202 may include the therapy delivery unit 212 that is configured to control generation of treatment stimulus provided to the electrodes 308 to provide an electrical stimulus to the tissue 304. In another particular embodiment, the medical device 202 is an implantable drug pump. In another particular embodiment, the medical device 202 is an implantable sensor. Examples of an implantable sensor may include an electrocardiogram (ESG) sensor, an electromyogram (EEG) sensor, etc. Note that the term "patient" is used broadly to include any organism and is not intended to imply that the patient 306 is human; although the patient 306 is a human patient in one embodiment.

Figure 4:
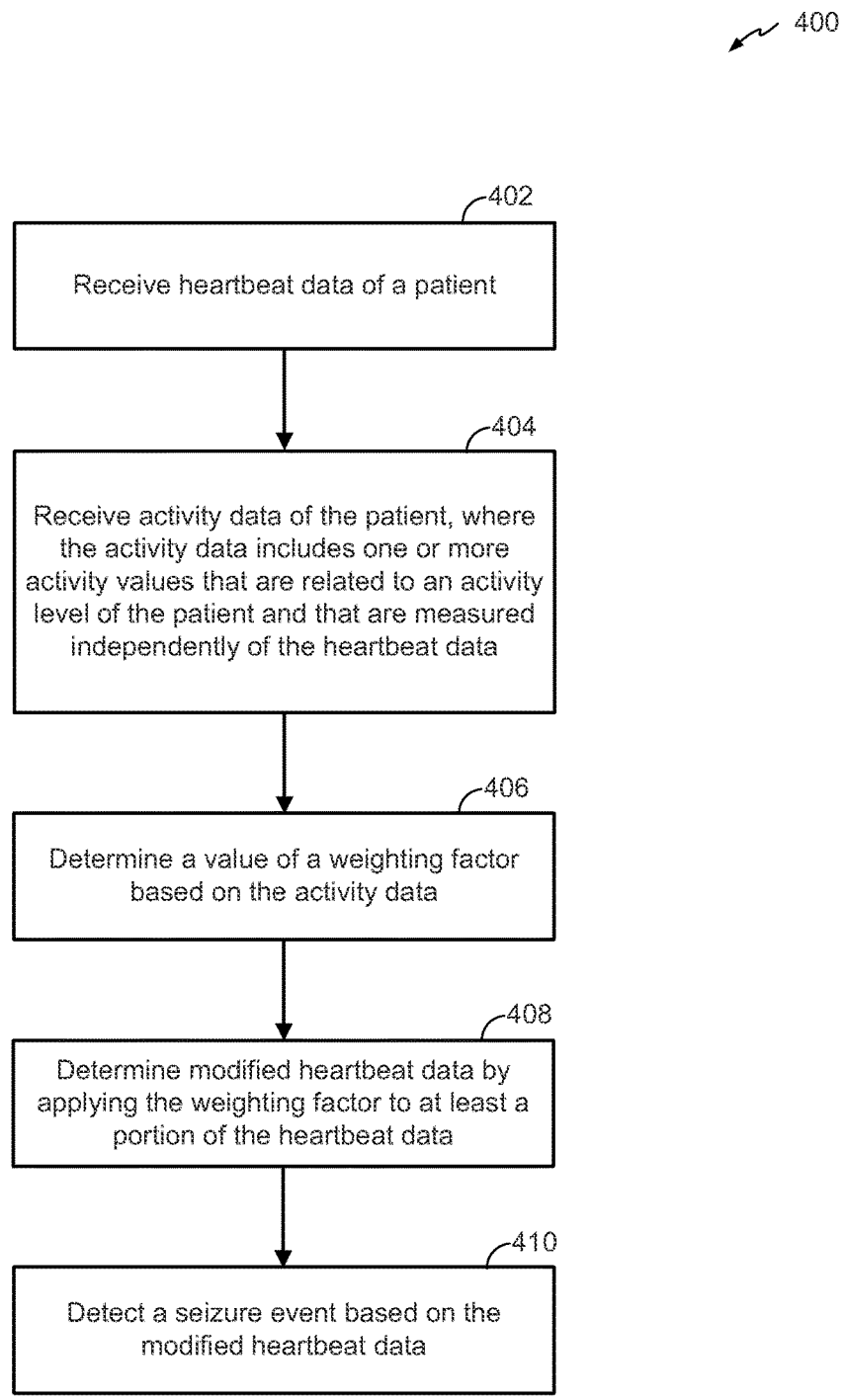
FIG. 4 is a flow chart of a particular embodiment of a method of detecting a seizure event based on heartbeat data and activity data.

FIG. 4 is a flow chart of a particular embodiment of a method 400 of detecting a seizure event based on heartbeat data and activity data. For example, the method 400 may be performed by a medical device and the components thereof, such as the medical device 202, the memory 204, the processor 206, the first interface 208, the second interface 210, the therapy delivery unit 212 of FIGS. 2 and 3, or any combination thereof. The method 400 may be performed while monitoring for a seizure event in a patient, such as the patient 306 of FIG. 3.

The method 400 may include receiving heartbeat data of a patient, at 402. For example, in FIG. 2, the first interface 208 may be coupled to receive the heartbeat data 220 of a patient, such as the patient 306 of FIG. 3. The heartbeat data 220 of the patient 306 may include electrocardiogram data (e.g., an electrocardiogram trace). For example, the heartbeat data 220 may correspond to the electrocardiogram illustrated in the first trace 110 of FIG. 1. The first interface 208 may provide the heartbeat data 220 to the processor 206.

Activity data of the patient may be received, at 404. For example, in FIG. 2, the second interface 210 may be coupled to receive the activity data 230. The activity data 230 may include one or more activity values that are related to an activity level of the patient 306 and that are measured independently of the heartbeat data 220. In a particular embodiment, the activity data 230 includes accelerometer data, body temperature data, electromyography data, perspiration data, impedance data, or a combination thereof. In a particular embodiment, the activity data 230 may be detected (e.g., sensed) by the activity sensor 330. Additionally or alternatively, the activity data 230 may be received wirelessly from one or more external sensors (not shown). The second interface 210 may provide the activity data 230 to the processor 206.

A value of a weighting factor may be determined based on the activity data, at 406. For example, in FIG. 2, the processor 206 may determine the value of the weighting factor such that an effect of prior heartbeat data on the modified heartbeat data is decreased in response to the activity data 230 indicating an increased activity level of the patient 306.

Modified heartbeat data may be determined by applying the weighting factor to at least a portion of the heartbeat data, at 408. For example, the processor 206 of FIG. 2 may determine the modified heartbeat data based on an algorithm, such as $BG_M = \lambda * BG_{n-1} + (1-\lambda) * FG_n$, where BGM is the modified heartbeat data (e.g., the modified background heart rate), $BG_{n-1}$ is a previously-determined background heart rate, $FG_n$ is a foreground heart rate at the present time (n), and $\lambda$ is the weighting factor determined based on the activity data. Thus, the modified heartbeat data may be determined as a sum of a first value and a second value. The first value ($\lambda * BG_{n-1}$) may be the weighting factor time the previously-determined background heart rate and the second value ($(1-\lambda) * FG_n$) may be one minus the weighting factor times the most recent R-R interval (e.g., the foreground heart rate).

A seizure event may be detected based on the modified heartbeat data, at 410. For example, the processor 206 of FIG. 2 may compare a ratio of the foreground heart rate and the modified background heart rate (e.g., the modified heartbeat data) to a seizure detection threshold. When the ratio exceeds the seizure detection threshold, the processor 206 may determine that a seizure event is present. When the ratio is below the seizure detection threshold, the processor 206 may determine that there is no seizure event present.

In a particular embodiment, the method 400 may include detecting an indication of noise in the heartbeat data. For example, the processor 206 of FIG. 2 may detect an indication of noise in the heartbeat data 220. The weighting factor may be further determined based on the indication of noise in the heartbeat data. For example, in response to the detected noise in the heartbeat data 220 increasing, the processor 206 may determine the value of the weighting factor such that an effect of prior heartbeat data on the modified heartbeat data is decreased. Thus, in response to the detected noise in the heartbeat data 220 increasing, the processor 206 may lower the value of the weighting factor so that the modified heartbeat data is more dependent on the foreground heart rate. Alternatively, in response to the detected noise in the heartbeat data decreasing, the processor 206 may determine the value of the weighting factor such that the effect of the prior heartbeat data on the modified heartbeat data is increased. Thus, in response to the detected noise in the heartbeat data 220 decreasing, the processor 206 may raise the value of the weighting factor so that the modified heartbeat data is more dependent on the previously-determined background heart rate.

In a particular embodiment, the method 400 may include causing stimulation to be applied to tissue of the patient in response to detecting the seizure event. For example, the therapy delivery unit 212 of FIG. 3 may control generation of treatment stimulus provided to the electrodes 308 to provide an electrical stimulus to the tissue 304 in response to the processor 206 detecting the seizure event. In another particular embodiment, the method 400 may include generating a report regarding the detection of a seizure event, and may include the initiation of a recording of a detected seizure event.

The illustrations of the embodiments described herein are intended to provide a general understanding of the structure of the various embodiments. The illustrations are not intended to serve as a complete description of all of the elements and features of apparatus and systems that utilize the structures or methods described herein. Many other embodiments may be apparent to those of skill in the art upon reviewing the disclosure. Other embodiments may be utilized and derived from the disclosure, such that structural and logical substitutions and changes may be made without departing from the scope of the disclosure. For example, method steps may be performed in a different order than is shown in the figures or one or more method steps may be omitted. Accordingly, the disclosure and the figures are to be regarded as illustrative rather than restrictive.

Moreover, although specific embodiments have been illustrated and described herein, it should be appreciated that any subsequent arrangement designed to achieve the same or similar results may be substituted for the specific embodiments shown. This disclosure is intended to cover any and all subsequent adaptations or variations of various embodiments. Combinations of the above embodiments, and other embodiments not specifically described herein, will be apparent to those of skill in the art upon reviewing the description.

The Abstract of the Disclosure is submitted with the understanding that it will not be used to interpret or limit the scope or meaning of the claims. In addition, in the foregoing Detailed Description, various features may be grouped together or described in a single embodiment for the purpose of streamlining the disclosure. This disclosure is not to be interpreted as reflecting an intention that the claimed embodiments require more features than are expressly recited in each claim. Rather, as the following claims reflect, the claimed subject matter may be directed to less than all of the features of any of the disclosed embodiments.

What is claimed is:

1. A method comprising:
   receiving heartbeat data of a patient;
   receiving accelerometer data of the patient;
   determining, using the accelerometer data, that the patient is transitioning from a sleep state to an awake state;
   decreasing a weighting factor based on the transition;
   determining modified heartbeat data by applying the weighting factor to at least a portion of the heartbeat data; and
   detecting a seizure event based on the modified heartbeat data.

2. The method of claim 1, wherein determining the modified heartbeat data includes determining a background (BG) heart rate based on a previously-determined BG heart rate, a most recent R-R interval, and the weighting factor.

3. The method of claim 2, wherein the BG heart rate is determined as a sum of a first value and a second value, wherein the first value is the weighting factor times the previously-determined BG heart rate and the second value is one minus the weighting factor times the most recent R-R interval.

4. The method of claim 2, wherein determining the modified heartbeat data further includes determining a foreground (FG) heart rate based on one or more R-R intervals of the heartbeat data.

5. The method of claim 4, wherein detecting the seizure event comprises comparing a ratio of the FG heart rate and the BG heart rate to a seizure detection threshold.

6. The method of claim 1, wherein the heartbeat data of the patient includes electrocardiogram data.

7. The method of claim 6, wherein the electrocardiogram data indicates a timing related to a plurality of R-waves.

8. The method of claim 1, further comprising causing, in response to the detection of the seizure event, initiation of at least one of a stimulation to tissue of the patient, a reporting of the occurrence of the seizure event, or a recording of the seizure event.

9. A medical device comprising:
a first interface to receive heartbeat data of a patient;
a second interface to receive acceleration data of the patient; and
a processor configured to:
determine, using the accelerometer data, that the patient is transitioning from a sleep state to an awake state;
decrease a weighting factor based on the transition;
determine modified heartbeat data by applying the weighting factor to at least a portion of the heartbeat data; and
detect a seizure event based on the modified heartbeat data.

10. The medical device of claim 9, wherein determining the modified heartbeat data includes determining a background (BG) heart rate based on a previously-determined BG heart rate, a most recent R-R interval, and the weighting factor.

11. The medical device of claim 10, wherein the BG heart rate is determined as a sum of a first value and a second value, wherein the first value is the weighting factor times the previously-determined BG heart rate and the second value is one minus the weighting factor times the most recent R-R interval.

12. The medical device of claim 10, wherein determining the modified heartbeat data further includes determining a foreground (FG) heart rate based on one or more R-R intervals of the heartbeat data, wherein the seizure event is detected by comparing a ratio of the FG heart rate and the BG heart rate to a seizure detection threshold.

13. The medical device of claim 9, wherein the processor, in response to the detection of the seizure event, provides a signal to at least one of stimulation device disposed to provide stimulation to tissue of the patient, a signal indicating the occurrence of the seizure event, and a signal initiating the recording of the seizure event.

14. A non-transitory computer-readable medium storing instructions that are executable by a processor to cause the processor to perform operations including:
receiving heartbeat data of a patient;
receiving accelerometer data of the patient;
determining, using the accelerometer data, that the patient is transitioning from a sleep state to an awake state;
decreasing a weighting factor based on the transition;
determining modified heartbeat data by applying the weighting factor to at least a portion of the heartbeat data; and
detecting a seizure event based on the modified heartbeat data.

15. The non-transitory computer-readable medium of claim 14, wherein determining the modified heartbeat data includes determining a background (BG) heart rate based on a previously-determined BG heart rate, a most recent R-R interval, and the weighting factor.

16. The non-transitory computer-readable medium of claim 15, wherein the BG heart rate is determined as a sum of a first value and a second value, wherein the first value is the weighting factor times the previously-determined BG heart rate and the second value is one minus the weighting factor times the most recent R-R interval.

17. The non-transitory computer-readable medium of claim 15, wherein determining the modified heartbeat data further includes determining a foreground (FG) heart rate based on one or more R-R intervals of the heartbeat data, wherein the seizure event is detected by comparing a ratio of the FG heart rate and the BG heart rate to a seizure detection threshold.

18. The non-transitory computer-readable medium of claim 14, wherein the processor, in response to the detection of the seizure event, provides a signal to at least one of stimulation device disposed to provide stimulation to tissue of the patient, a signal indicating the occurrence of the seizure event, and a signal initiating the recording of the seizure event.

* * * * *